US012733873B2

(12) United States Patent
Koskimäki

(10) Patent No.: US 12,733,873 B2
(45) Date of Patent: Sep. 15, 2026

(54) TECHNIQUES FOR MIGRAINE DETECTION USING A WEARABLE DEVICE

(71) Applicant: Oura Health Oy, Oulu (FI)

(72) Inventor: Heli Tuulia Koskimäki, Oulu (FI)

(73) Assignee: Oura Health Oy, Oulu (FI)

( * ) Notice: Subject to any disclaimer, the term of this patent is extended or adjusted under 35 U.S.C. 154(b) by 208 days.

(21) Appl. No.: 18/612,879

(22) Filed: Mar. 21, 2024

(65) Prior Publication Data

US 2025/0295357 A1 Sep. 25, 2025

(51) Int. Cl.
*A61B 5/00* (2006.01)
*A61B 5/024* (2006.01)

(52) U.S. Cl.
CPC ........ *A61B 5/4815* (2013.01); *A61B 5/02416* (2013.01); *A61B 5/4812* (2013.01); *A61B 5/6802* (2013.01)

(58) Field of Classification Search
None
See application file for complete search history.

(56) References Cited

U.S. PATENT DOCUMENTS 10,878,691 B1 12/2020 McLendon et al.
10,943,696 B2 3/2021 Demestichas et al.
11,887,729 B2 1/2024 McLendon et al.
12,183,464 B2 12/2024 Aronovich et al.
12,354,752 B2 7/2025 Jaiswal et al.
2021/0169417 A1* 6/2021 Burton ................. A61B 5/4857
2022/0054040 A1* 2/2022 Pho ...................... A61B 5/4812
2022/0110547 A1* 4/2022 Kinnunen .......... A61B 5/02416
2022/0409187 A1 12/2022 Pho et al.
(Continued)

FOREIGN PATENT DOCUMENTS

CN 119700054 A 3/2025
CN 116251280 B 11/2025
(Continued)

OTHER PUBLICATIONS

"International Search Report and Written Opinion of the International Searching Authority,"issued in connection with Int'l Appl. No. PCT/US2025/020956, dated Jun. 18, 2025 (12 pages).
(Continued)

*Primary Examiner* — Amanda K Hulbert
(74) *Attorney, Agent, or Firm* — ArentFox Schiff LLP

(57) ABSTRACT

Methods, systems, and devices for migraine detection are described. The described techniques may enable a wearable device to analyze collected physiological data to predict when a user may experience a migraine. In some examples, users may experience a decrease in total sleep time, a decrease in REM sleep, and a decrease in body temperature during one or more days prior to onset of migraine symptoms. Accordingly, a wearable device may use these physiological features observed within sleep data and temperature data collected via a wearable device to predict that a user will experience a migraine based on a comparison to baseline values. Such migraine prediction techniques may enable users to take medications prior to symptom onset, which may reduce a severity of the migraine symptoms. In some examples, the wearable device may utilize other physiological data to predict migraine onset.

20 Claims, 6 Drawing Sheets

(56) References Cited

U.S. PATENT DOCUMENTS

| | | | | |
|---|---|---|---|---|
| 2023/0277123 | A1 * | 9/2023 | Griffin ................. | A61B 5/4842 381/74 |
| 2024/0164724 | A1 * | 5/2024 | Rautakoski .......... | A61B 5/0205 |

FOREIGN PATENT DOCUMENTS

| | | | |
|---|---|---|---|
| CN | 121264984 | A | 1/2026 |
| CN | 121621950 | A | 3/2026 |
| IN | 202221039456 | A | 1/2024 |
| IN | 202441094894 | A | 12/2024 |
| IN | 202421095611 | A | 1/2025 |
| IN | 202541015516 | A | 3/2025 |
| IN | 202541121973 | A | 1/2026 |
| IN | 202541129972 | A | 2/2026 |
| IN | 202641001610 | A | 3/2026 |
| WO | 2016/156171 | A1 | 10/2016 |
| WO | 2018/093549 | A1 | 5/2018 |

OTHER PUBLICATIONS

Houle, T. T., et al., “Stress and sleep duration predict headache severity in chronic headache sufferers”, Pain, vol. 153, No. 12, Dec. 1, 2012, pp. 2432-2440.

Kim, S. H., et al., “The influence of rapid eye movement sleep deprivation on nociceptive transmission and the duration of facial allodynia in rats: a behavioral and Fos immunohistochemical study.”, Thejournal of headache and pain, vol. 20, Mar. 1, 2019, pp 1-9.

Stanyer, E. C., et al., “Investigating the relationship between sleep and migraine in a global sample: a Bayesian cross-sectional approach”, The Journal of Headache and Pain, vol. 24, No. 1, Sep. 8, 2023, 13 pages.

Stubberud, A., et al., “Forecasting migraine with machine learning based on mobile phone diary and wearable data”, Cephalalgia, vol. 43, No. 5, Apr. 25, 2023, 10 pages.

* cited by examiner

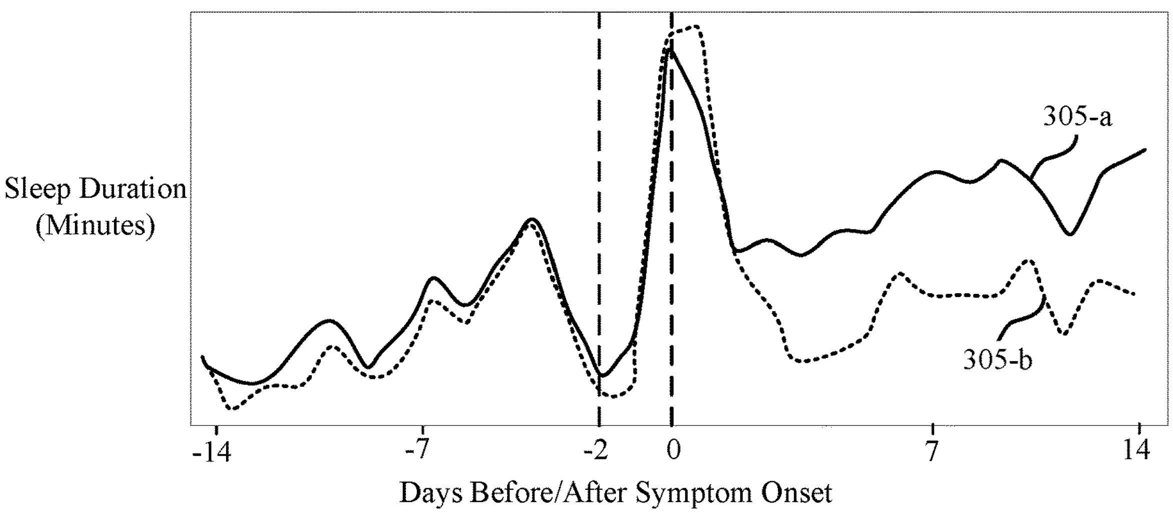
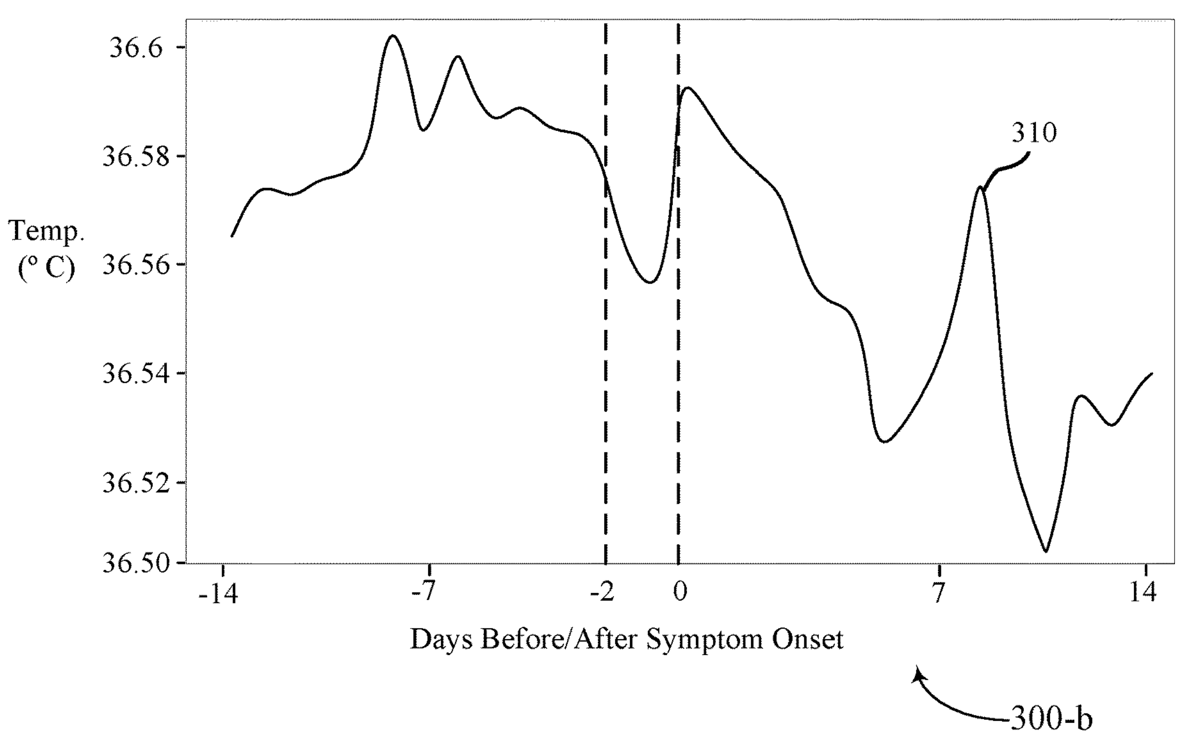
FIG. 3

Figure 5:
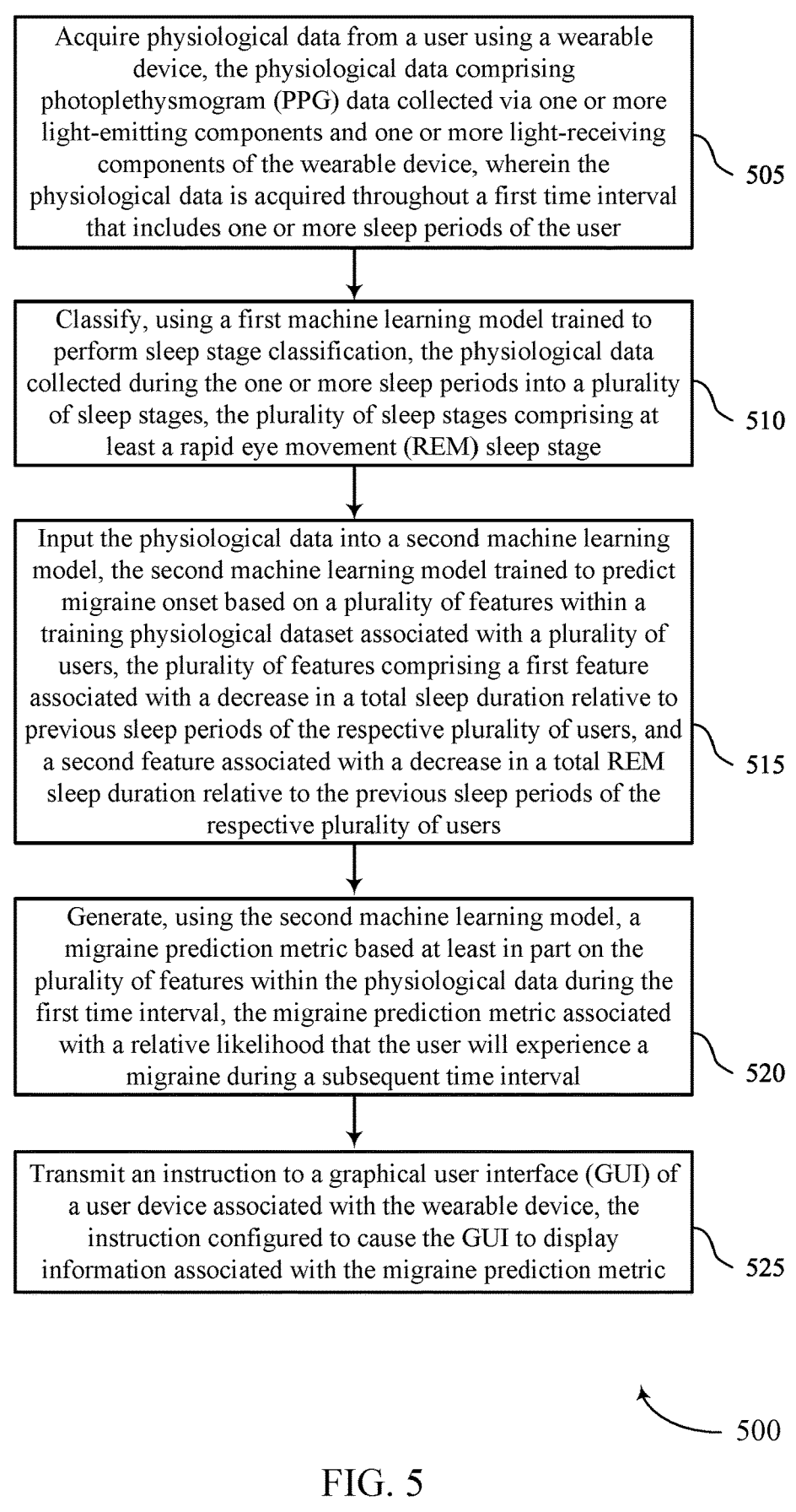

Acquire physiological data from a user using a wearable device, the physiological data comprising photoplethysmogram (PPG) data collected via one or more light-emitting components and one or more light-receiving components of the wearable device, wherein the physiological data is acquired throughout a first time interval that includes one or more sleep periods of the user

505

Classify, using a first machine learning model trained to perform sleep stage classification, the physiological data collected during the one or more sleep periods into a plurality of sleep stages, the plurality of sleep stages comprising at least a rapid eye movement (REM) sleep stage

510

Input the physiological data into a second machine learning model, the second machine learning model trained to predict migraine onset based on a plurality of features within a training physiological dataset associated with a plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users

515

Generate, using the second machine learning model, a migraine prediction metric based at least in part on the plurality of features within the physiological data during the first time interval, the migraine prediction metric associated with a relative likelihood that the user will experience a migraine during a subsequent time interval

520

Transmit an instruction to a graphical user interface (GUI) of a user device associated with the wearable device, the instruction configured to cause the GUI to display information associated with the migraine prediction metric

TECHNIQUES FOR MIGRAINE DETECTION USING A WEARABLE DEVICE

FIELD OF TECHNOLOGY

The following relates to wearable devices and data processing, including techniques for migraine detection using a wearable device.

BACKGROUND

Some wearable devices may be configured to collect data from users associated with temperature data, sleep time data, heart rate data, and the like. Some users may use the collected data for health insights.

BRIEF DESCRIPTION OF THE DRAWINGS

FIG. 3 shows an example of a data diagrams that supports techniques for migraine detection using a wearable device in accordance with aspects of the present disclosure.

FIGS. 5 and 6 show flowcharts illustrating methods that support techniques for migraine detection using a wearable device in accordance with aspects of the present disclosure.

DETAILED DESCRIPTION

Figure 1:
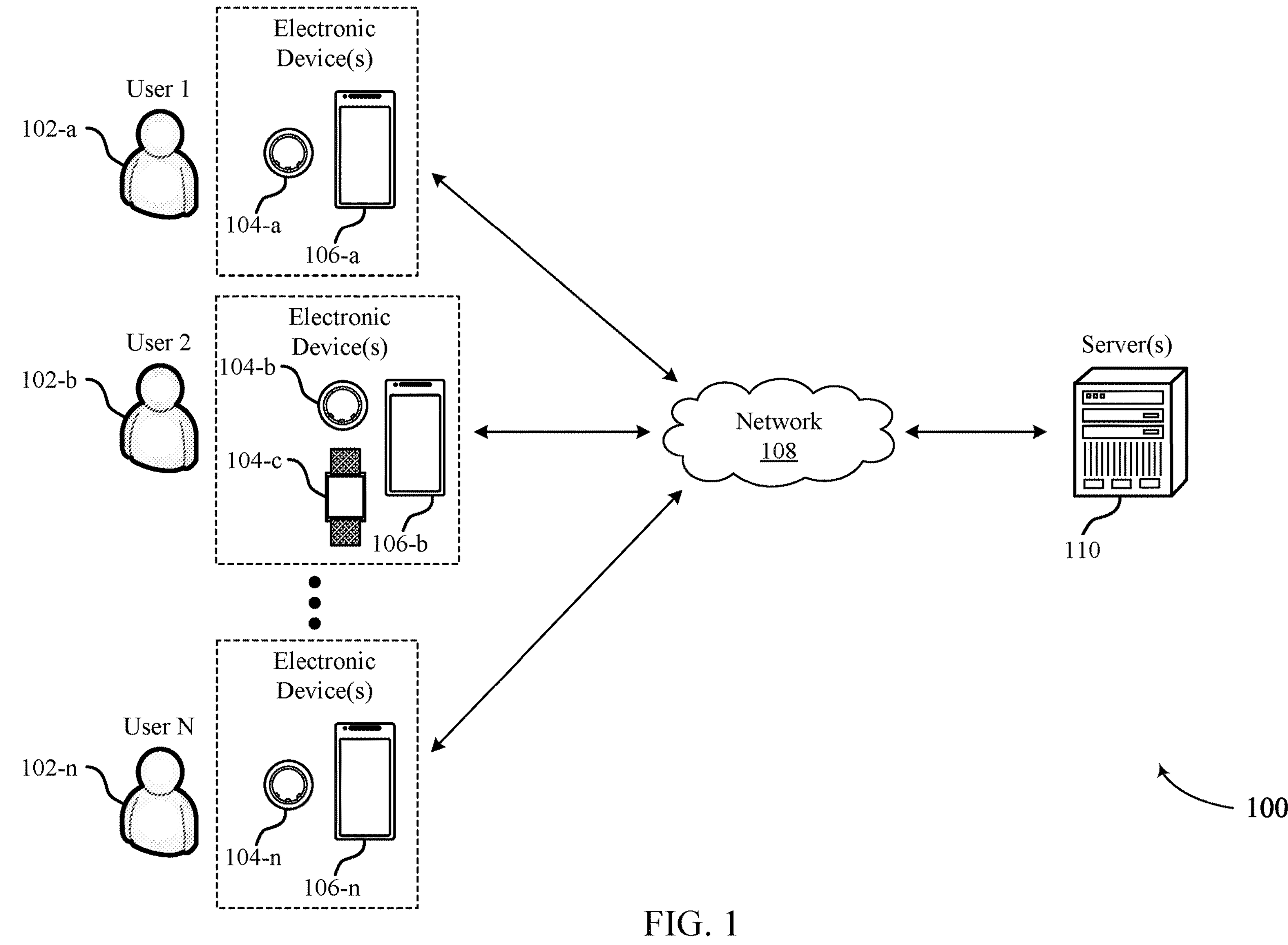
FIG. 1 illustrates an example of a system that supports techniques for migraine detection using a wearable device in accordance with aspects of the present disclosure.

Wearable devices may be configured to collect physiological data from users to provide users with information regarding their sleep patterns and overall health. Physiological data collected from wearable devices may include sleep data, heart rate data, temperature data, and the like. In some cases, a user of a wearable device may experience migraines. The user may take medications to alleviate migraine symptoms on an as-needed basis (e.g., when migraine symptoms first appear, rather than taking such medications every day as a preventative measure). However, migraine medications may be relatively less effective when taken after the migraine symptoms have already started. That is, migraine medications may be relatively more effective when taken prior to onset of migraine symptoms. However, the user may not be able to predict a day or time at which the users may experience a migraine prior to symptom onset, and conventional wearable devices may be unable to perform such migraine prediction.

Accordingly, techniques described herein may enable a wearable device to analyze collected physiological data to predict when a user may experience a migraine. In particular, the wearable device may analyze previously-collected physiological data (e.g., data collected during a time period prior to a previous migraine) to predict when a user may experience a migraine in the future. In some examples, users may experience physiological changes such as a decrease in total sleep time, a decrease in rapid eye movement (REM) sleep, and a decrease in body (e.g., skin) temperature during one or more days prior to onset of migraine symptoms. Moreover, such physiological changes generally occur at approximately a same time prior to symptom onset (e.g., approximately two days prior to symptom onset). As such, in some cases, techniques described herein may utilize machine learning models that are trained to predict migraine onset based on specific features (e.g., decrease in total sleep, decrease in REM sleep) that may be observed within physiological data prior to migraine onset.

Accordingly, a wearable device (e.g., or a user device that is coupled with the wearable device) may use these physiological features observed within sleep data and temperature data collected via a wearable device to predict that a user will experience a migraine in the coming days (e.g., based on a comparison to baseline values). Such migraine prediction techniques may enable users to take medications at certain times (e.g., prior to symptom onset), which may prevent the migraine and/or reduce a severity of the migraine symptoms. In some examples, the wearable device may utilize other features or changes to predict migraine onset, such as a duration since a previous migraine, stress levels, heart rate or heart rate variability, taggable events, and so on.

In some aspects, the wearable device may cause a graphical user interface (GUI) to display one or more messages to the user in response to predicting the onset of migraine symptoms. For example, the wearable device may provide a recommendation for the user to take migraine medication. In some examples, the wearable device may cause a different GUI (e.g., a GUI associated with a caretaker of the user) to display the one or more messages. In some examples, the GUI may provide a prompt for the user to add a "tag" that indicates the onset of migraine symptoms. Such techniques may allow for the wearable device to provide relatively more accurate migraine predictions.

Aspects of the disclosure are initially described in the context of systems supporting physiological data collection from users via wearable devices. Aspects of the disclosure are further illustrated by and described with reference to data diagrams and GUIs.

FIG. 1 illustrates an example of a system 100 that supports techniques for migraine detection using a wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols. Moreover, in some cases, the wearable device 104 and the user device 106 may be included within (or make up) the same device. For example, in some cases, the wearable device 104 may be configured to execute an application associated with the wearable device 104, and may be configured to display data via a GUI.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, as described herein, the sleep stage classification techniques may be utilized to predict an onset of migraine symptoms. For example, the system 100 may utilize the classifier (e.g., or another classifier or machine learning model) to determine a total sleep time (e.g., including a sum of respective durations of the REM sleep state, the light sleep stage, and the deep stage) and an REM sleep time (e.g., the duration of the REM sleep stage). The system 100 may accordingly predict an onset of migraine symptoms (e.g., using an algorithm or machine learning model) based on correlating respective decreases in both of the total sleep time and the REM sleep time (e.g., and one or more other physiological changes, such as a decrease in body temperature).

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques analyzing collected physiological data to predict when a user 102 may experience a migraine. In particular, the system 100 may analyze previously-collected physiological data (e.g., data collected during a time period prior to a previous migraine) to predict when a user 102 may experience a migraine in the future. In some examples, users 102 may experience physiological changes such as a decrease in total sleep time, a decrease in REM sleep, and a decrease in body temperature during one or more days prior to onset of migraine symptoms. Moreover, such physiological changes generally occur at approximately a same time prior to symptom onset (e.g., approximately two days prior to symptom onset).

Accordingly, the system 100 (e.g., a wearable device 104 or a user device 106 that is coupled with the wearable device 104) may use these physiological features observed within sleep data and temperature data collected via a wearable device to predict that a user 102 will experience a migraine in the coming days (e.g., based on a comparison to baseline values). Such migraine prediction techniques may enable users 102 to take medications at certain times (e.g., prior to symptom onset), which may prevent the migraine and/or reduce a severity of the migraine symptoms. In some examples, the wearable device 104 may utilize other features or changes to predict migraine onset, such as a duration since a previous migraine, stress levels, heart rate or heart rate variability, taggable events, and so on.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
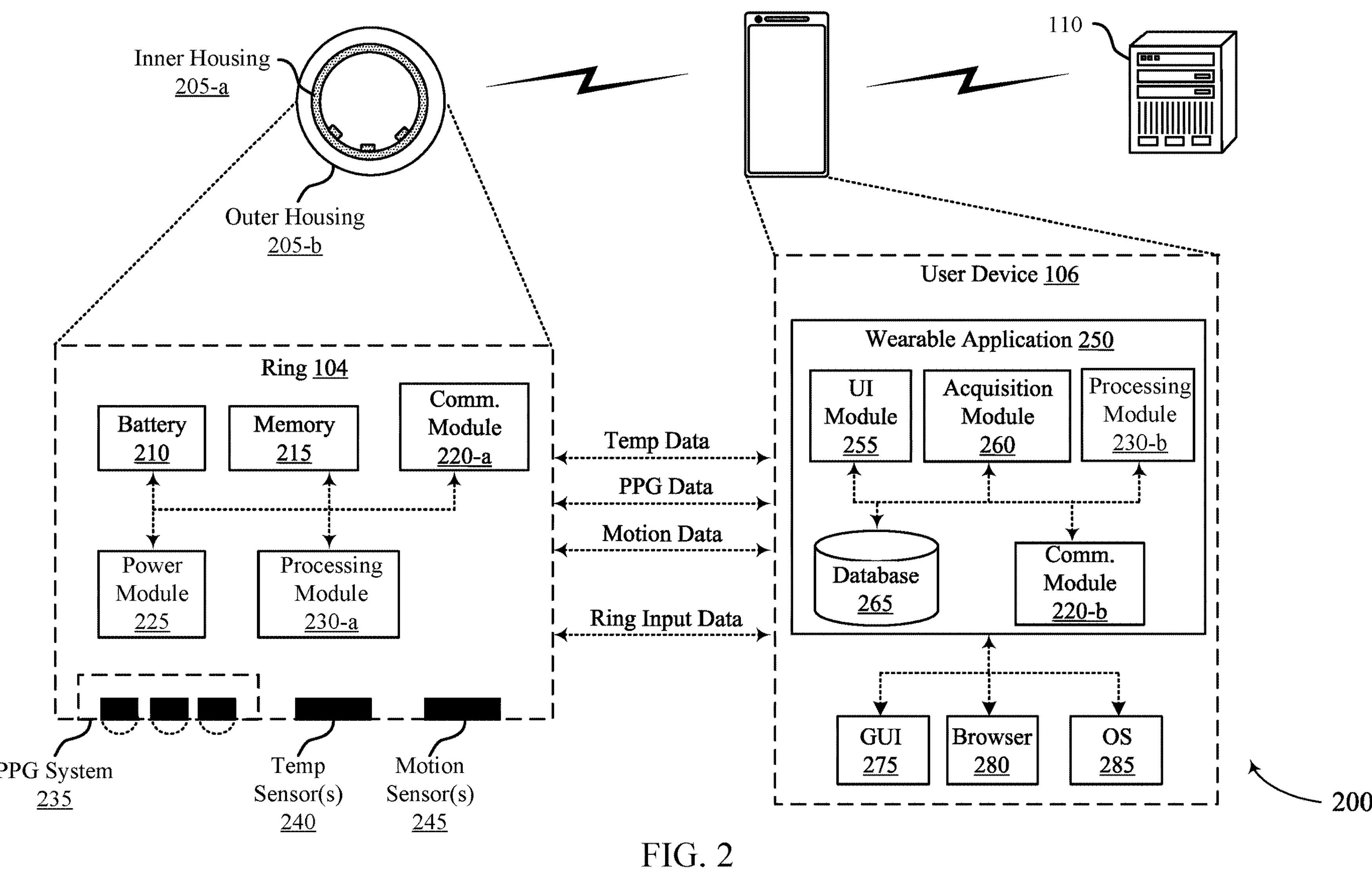
FIG. 2 illustrates an example of a system that supports techniques for migraine detection using a wearable device in accordance with aspects of the present disclosure.

FIG. 2 illustrates an example of a system 200 that supports techniques for migraine detection using a wearable device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals.

For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

In some cases, the wearable device 104 and the user device 106 may be included within (or make up) the same device. For example, in some cases, the wearable device 104 may be configured to execute the wearable application 250, and may be configured to display data via the GUI 275. In some aspects, the wearable device 104 may cause the GUI 275 to display one or more messages related to migraine prediction via the GUI 275.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

Some examples of the system 200 may enable users to input "tags" or other otherwise input indications of certain events, activities, or conditions via a mobile device (e.g., a GUI 275 of a user device 106). Taggable events may include, but are not limited to, alcohol consumption, caffeine consumption, travel, a workout, late night meal, illnesses, and so on. Inputting such tags may enable a system to gain insights regarding how a behavior or action of a user may affect physiological data associated with the user. For example, if a user tags caffeine consumption in the late afternoon, and subsequently suffers from poor sleep quality that night, the system may be able to conclude that the poor sleep quality is due to late caffeine consumption, and may therefore suggest that the user reduce their caffeine consumption or adjust a timing of their caffeine consumption in order to improve their sleep quality.

In some aspects, the system 200 may support techniques for analyzing collected physiological data to predict when a user may experience a migraine. In particular, the system 200 may analyze previously-collected physiological data (e.g., data collected during a time period prior to a previous migraine, and/or physiological data collected from other users) to predict when a user may experience a migraine in the future. The system 200 may utilize the previously-collected data and/or one or more taggable events (e.g., a migraine tag) input by the user or one or more other users to train a model (e.g., a machine learning model). In this regard, the trained machine learning model may be used to predict migraine onset based on specific features (and relationships between features) observed within the physiological data used to train the model. For example, users may experience physiological changes such as a decrease in total sleep time, a decrease in REM sleep, and a decrease in body temperature during one or more days prior to onset of migraine symptoms. These physiological phenomena and behaviors may be referred to as "features" that are used to predict migraine onset. The system 200 may determine the decrease in total sleep time and/or REM sleep time based on physiological data collected via a ring 104 and sleep stage classifying techniques described herein. Moreover, such physiological changes generally occur at approximately a same time prior to symptom onset (e.g., approximately two days prior to symptom onset). In this regard, a machine learning model may be used to predict symptom onset based on the presence (or absence) of specific features, as well as a relationship between features (e.g., based on two features occurring at approximately the same time, such as a decrease in total sleep and a decrease in REM sleep happening on the same day or consecutive days).

Accordingly, the system 200 (e.g., a ring 104 or a user device 106) may use these physiological features observed within sleep data and temperature data collected via a wearable device to predict that a user 102 will experience a migraine in the coming days (e.g., based on a comparison to baseline values). Such migraine prediction techniques may enable users 102 to take medications at certain times (e.g., prior to symptom onset), which may prevent the migraine and/or reduce a severity of the migraine symptoms. In some examples, the wearable device 104 may utilize other features or changes to predict migraine onset, such as a duration since a previous migraine, stress levels, heart rate or heart rate variability, taggable events, and so on. Such techniques are described herein in further detail with reference to FIG. 3.

In some aspects, the system 200 may cause a GUI 275 of a user device 106 (e.g., a user device associated with the user or a caretaker of the user) to display one or more messages to the user in response to predicting the onset of migraine symptoms. For example, the system 200 may provide a recommendation for the user to take migraine medication. In some cases, the system may "learn" when medications are most effective for mitigating migraine symptoms based on previous migraines experienced by the user, and may therefore recommend specific times for taking such medications. In some examples, the GUI 275 may provide a prompt for the user to add a taggable event that indicates the onset of migraine symptoms. Such techniques are described herein in further detail with reference to FIG. 4.

FIG. 3 shows examples of data diagrams 300-*a* and 300-*b* that support techniques for migraine detection using a wearable device in accordance with aspects of the present disclosure. The data diagrams 300-*a* and 300-*b* may implement, or be implemented by, aspects of the system 100 and/or the system 200. For example, the data illustrated by the data diagrams 300 may be collected by a wearable device, and the one or more devices of the system 100 and/or the system 200 may utilize data diagrams such as the data diagrams 300-*a* and 300-*b* to provide insights to a user, such as a message related to migraine prediction.

The x-axis of the respective data diagrams 300-*a* and 300-*b* illustrates a time (e.g., in days) before and after symptom onset (e.g., before/after the user experiences a migraine), where the vertical reference lines at time 0 may illustrate an onset of migraine symptoms for the user. The vertical reference line at time −2 may illustrate metrics of a user two days prior to the onset of migraine symptoms. The y-axis of the data diagram 300-*a* illustrates a time duration of sleep for the user (e.g., a duration of total sleep or REM sleep for the user). The y-axis of the data diagram 300-*b* illustrates a body temperature of the user (e.g., a skin temperature in degrees Celsius).

In some aspects, a system (e.g., a system including a wearable ring device and/or a wrist-worn wearable device and a user device, such as the system 100 and the system 200) may detect periods of time that a user is asleep, and classify periods of time that the user is asleep into one or more sleep stages (e.g., sleep stage classification). For example, a wearable device may collect physiological data (e.g., PPG data collected via one or more light-emitting components and light-receiving components of the wearable device and/or temperature data collected via one or more temperature sensors of the wearable device as described herein) associated with a user, including temperature, heart rate, HRV, respiratory rate, and the like. The wearable device may collect the data during a time interval that includes one or more sleep periods of the user. For example, as illustrated with reference to the data diagram 300-*a* and the data diagram 300-*b*, the wearable device may collect the data during a time interval of 29 days (e.g., including during sleep periods during the 29 days), including 14 days prior to migraine symptom onset and 14 days following migraine symptom onset.

In some aspects, the wearable device may transmit the collected physiological data to a user device (or other device, such as servers) for processing. That is, a user device may receive the physiological data via one or more electronic signals from the wearable device. The system may input some or all of the physiological data into a machine learning classifier, where the machine learning classifier is configured to determine periods of time that the user is (or was) asleep. In some examples, the machine learning classifier may be trained based on a training data set measured from the user and/or a plurality of users (e.g., during one or more time period prior to the measurement time interval). In this regard, the training data set may include physiological data associated with the user and/or other users during periods of time that the user and/or other users were asleep.

Moreover, the machine learning classifier may be configured (e.g., trained) to perform sleep stage classification to classify periods of time into different sleep stages, including an awake sleep stage, a REM sleep stage, a light sleep stage, and a deep sleep stage. Accordingly, the training data set may include physiological data associated with the user and/or the other users during periods of REM sleep, light sleep, and deep sleep. The user device may operate the machine learning classifier via one or more processors of the user device. In some aspects, as described previously herein, classifying sleep data into one or more sleep stages may be based on a circadian rhythm associated with each respective user.

By classifying the physiological data into different sleep stages, the system may generate a data set such as the example data illustrated with reference to the data diagram 300-*a*. That is, the system may generate a dataset including the REM sleep time 305-*a* and total sleep time 305-*b* during each of the one or more sleep periods of the user throughout the time interval.

In some aspects, the system may input the classified physiological data into a second machine learning model that is trained to predict migraine onset based on one or more features. That is, the system may input data associated with REM sleep time 305-*a* (e.g., a duration that the user experienced REM sleep during each of one or more sleep periods in the time interval) and data associated with total sleep time 305-*b* (e.g., a total duration that the user experienced sleep during each of the one or more sleep periods in the time interval) into a second machine learning model. The second machine learning model may be trained to predict migraine onset (e.g., a probability of migraine onset, a time of migraine onset) based on specific features (and/or relationships between features) within the physiological data. Features that may be used by the machine learning model to predict migraine onset may include a first decrease in a total sleep duration during a first sleep period relative to previous sleep periods, and a second decrease in an REM sleep duration during the first sleep period relative to the previous sleep periods.

The second machine learning model may be trained based on a training physiological dataset associated with a plurality of users (e.g., users that experience migraines). For example, the training physiological dataset may include sleep data of the plurality of users during one or more sleep periods leading up to migraine onset. The training physiological dataset may include a first decrease in a total sleep duration of the plurality of users during a first sleep period relative to previous sleep periods of the plurality of users and a second decrease in an REM sleep duration during the first sleep period of the plurality of users relative to the previous sleep periods of the plurality of users. In other words, the second machine learning model may be trained using the physiological dataset to identify migraine onset based on decreases in total sleep duration and decreases in REM sleep for the respective users.

In some examples, the system may input additional physiological data measured by the wearable device, such as temperature data 310 (e.g., or data related to menstrual cycles, stress, heart rate, or heart rate variability) into the second machine learning model. In this regard, the second machine learning model may be configured to predict migraine onset using temperature-related features, stress-related features, heart rate-related features, HRV-related features, or any combination thereof. For example, the features used to predict migraine onset may include a third decrease in temperature data relative to baseline temperature data (e.g., or one or more other features for predicting migraine onset related to the additional physiological data). That is, the training physiological dataset may include temperature data of the plurality of users, including a decrease in temperature data of the plurality of users relative to baseline temperature data of the plurality of users (e.g., or data related to the one or more other features).

In some cases, the second machine learning model may be trained to predict migraine onset based on features observed within physiological data collected from a group of users, and may be subsequently trained/refined to predict migraine onset based on features collected by each respective user. In other words, the second machine learning model may be "tailored" to predict migraine onset based on specific physiological features for the user.

It has been found that the presence (or absence) of individual features may not be overly useful in predicting migraine onset. However, migraines may be predicted with much greater accuracy when combining multiple features together. As such, in addition to predicting migraine onset based on the presence (or absence) of specific features, the second machine learning model may be configured to predict migraine onset based on combinations of features being present at the same time, and/or a temporal relationship between specific features. In other words, the second machine learning model may be configured to predict migraine onset based on specific features occurring at approximately the same time (e.g., within the same day, within the same night of sleep, within consecutive days, etc.). For instance, as shown in the data diagram 300-*a*, it has been found that users generally experience a decrease in total sleep and a decrease in REM sleep at approximately the same time (e.g., ~2 days prior to migraine onset). Moreover, as shown in the data diagram 300-*b*, users typically experience a decrease in temperature at approximately the same time as the decrease in total sleep and a decrease in REM sleep (e.g., ~2 days prior to migraine onset). In this regard, while any one of these individual features may not be overly predictive of migraine onset on their own, the occurrence of these respective features at approximately the same time (e.g., within 24 hours of one another) has been found to be highly predictive of migraine onset.

In this regard, the training physiological dataset may include the decrease in temperature, the decrease in REM sleep time, and the decrease in total sleep time during correlated time periods. That is, the plurality of users may each experience the first decrease, the second decrease, and the third decrease during a same time period (e.g., two days prior to migraine onset).

The second machine learning model may generate a migraine prediction metric (e.g., a likelihood or probability that a user may experience a migraine during a subsequent time interval) based on the plurality of features. For example, the second machine learning model may determine the migraine prediction metric based on respective decreases (e.g., a decrease in total sleep time 305-*b*, a decrease in REM sleep time 305-*a* and/or a decrease in body temperature data 310) occurring at approximately a same time. As described herein, the features may be said to occur at "approximately the same time" if the features occur during a same day (e.g., during a same sleep period or sleep day), during sequential days (e.g., during sequential sleep periods), or within a threshold time period from one another. In some examples, the second machine learning model may generate the migraine prediction metric based on duration and/or magnitude of the respective decreases (e.g., in addition to or instead of the timing of the respective decreases). Further, the machine learning model may be configured to "learn" other features that may be used to predict migraine onset for the respective user.

In some examples, the second machine learning model may determine an estimation of the subsequent time interval associated with the migraine onset (e.g., the time interval during which the migraine is predicted to occur). For example, the second machine learning model may output a day during which the user may experience the migraine (e.g., with a likelihood associated with the migraine prediction metric) based on the plurality of features. For instance, referring to the example above, the second machine learning model may observe the respective features (e.g., decrease in total sleep, decrease in REM sleep, decrease in temperature) on Tuesday (e.g., day −2), and may therefore predict that the user will experience a migraine on Thursday (e.g., day 0).

In some examples, the second machine learning model may generate the migraine prediction metric and/or the subsequent time interval based on a time between migraine attacks (e.g., an average time between migraine attacks associated with the user and/or the plurality of users) and a time associated with one or more previous migraine attacks. In other words, the machine learning model may predict that a user will experience a migraine based on how long its been since the user's previous migraine attack, and the average time between migraine attacks for the user. For example, if a time between a prior migraine attack and a current time is within a threshold time of the average time between migraine attacks, the second machine learning model may determine that a migraine attack in the subsequent time interval is relatively more likely.

As an illustrative example, as shown with reference to the data diagram 300-*a*, the second machine learning model may determine (e.g., based on the training physiological dataset) that a correlated decrease in both of REM sleep time 305-*a* and total sleep time 305-*b* may be indicative of migraine onset. For example, the second machine learning model may determine that a decrease in both of REM sleep time 305-*a* and total sleep time 305-*b* at a day D=−2 (e.g., and a day D=−1) may be indicative of a migraine onset occurring at D=0. In some examples, the second machine learning model may determine that a correlated decrease (e.g., during a same time period, during sequential time periods, within a threshold time period) in REM sleep time 305-*a*, total sleep time 305-*b*, and body temperature 310 may be indicative of migraine onset. While the individual characteristics and parameters illustrated in FIG. 3 may be somewhat noisy individually, these respective parameters may be used to effectively predict migraines when taken together or as a combination. For example, a correlated decrease in total sleep time, REM sleep time, and/or body temperature of a user may indicate that the user may experience migraine symptoms at a future time (e.g., two days in the future).

In some aspects, one or more factors may affect the physiological data (e.g., factors other than onset of migraines). Accordingly, the second machine learning model may apply one or more predictive weights to the plurality of features (e.g., to generate a relatively more accurate migraine prediction metric). Predictive weights may be based on hormonal factors, predictable patterns or cycles (e.g., menstrual cycle, seasonal cycle, weekly cycle, etc.), and the like.

For example, a menstrual cycle of the user may impact one or more of the body temperature of the user and a likelihood that the user may experience a migraine. In other words, temperature swings may be more or less indicative of a migraine depending on where the user is within their menstrual cycle. Accordingly, the system may generate a menstrual cycle model (e.g., based on menstrual cycle data associated with the user) and input the menstrual cycle model into the second machine learning model. The machine learning model may apply a predictive weight to the feature associated with a decrease in temperature when generating the migraine prediction metric based on the menstrual cycle model.

Further, the system may be configured to account for or otherwise consider hormonal factors that may affect a user's susceptibility to migraines. For example, during the user's menstrual cycle, the user may experience a drop in estrogen just before the user's period, which may be a cause for a migraine attack. For instance, due to hormonal factors, migraines may be most likely to develop in either the two days leading up to the user's period, or the three days following a completion of the user's period. This may be due to the natural drop in estrogen levels at these times depending on the specific user.

Hormonal migraines/headaches may also be caused by other hormonal triggers unrelated to the user's menstrual cycle/periods. Hormone-related migraines and attacks are typically more severe than migraines caused by other triggers and/or experienced at other times of the month, and may be more likely to come back the following day. As such, machine learning models, algorithms, and other migraine-prediction techniques described herein may be trained to take this into account by adding predictive weights for predicting migraine onset depending on the user's hormonal cycles or other hormonal triggers. For example, if the system predicts/identifies that the user has experienced (or is likely to experience) a migraine that is likely attributable to hormonal related factors (e.g., based on the timing of the migraine relative to the user's menstrual cycle, for example), the system may further apply a predictive weight for predicting migraine onset the following day. In other words, the system may determine that it is more likely that the user will experience a migraine the day following a hormone-related migraine.

In some aspects, the system may determine a time interval for performing one or more preventative measures based on the timing of the plurality of features and the estimated timing of the migraine onset. For example, the system may determine a time interval for the user to take one or more preventative migraine medications (e.g., following the decrease in total sleep time 305-*b*, REM sleep time 305-*a*, and body temperature 310) prior to the estimated timing of the migraine onset. The system may determine the time interval using data related to migraine medication effectiveness based on timing of migraine medication administration. The system may determine the time interval using an algorithm or machine learning model (e.g., a machine learning model trained based on the data related to migraine effectiveness based on timing of migraine medication administration). In some cases, the system may "learn" when medications are most effective for mitigating migraine symptoms based on previous migraines experienced by the user, and may therefore recommend specific times for taking such medications.

Based on generating the migraine prediction metric, the system may transmit an instruction to cause a GUI of the user device (e.g., or another user device) to display one or more messages (e.g., information associated with the migraine prediction metric) to the user, as described in further detail with reference to FIG. 4. For example, the system may transmit an instruction for the GUI to display the estimation of the subsequent time interval (e.g., the time interval during which the user may experience a migraine) and/or the time interval for performing preventative measures. The system may transmit the instruction based on the migraine prediction metric being above a threshold migraine prediction metric. By generating the migraine prediction metric and displaying the messages via the GUI prior to onset of migraine symptoms, the system may decrease a severity of migraine symptoms (e.g., by providing recommendations to the user such as the time interval for performing preventative measures).

In some examples, the system may train the second machine learning model based on baseline physiological data associated with the user. For example, the system may measure the baseline physiological data (e.g., via the wearable device) during a time prior to the measurement time interval. The user may input one or more tags associated with the baseline physiological data indicating that the user experienced a migraine during the time prior to the measurement time interval. The system may therefore train the second machine learning model based on the baseline physiological data and the received tags. That is, the second machine learning model may identify that features in physiological data similar to features in the baseline physiological data (e.g., decreases in total sleep time, REM sleep time, and/or body temperature detected within the baseline physiological data) is indicative of a migraine. The second machine learning model may therefore use a comparison of the baseline physiological data and the data collected during the measurement time interval to generate the migraine prediction metric.

Figure 4:
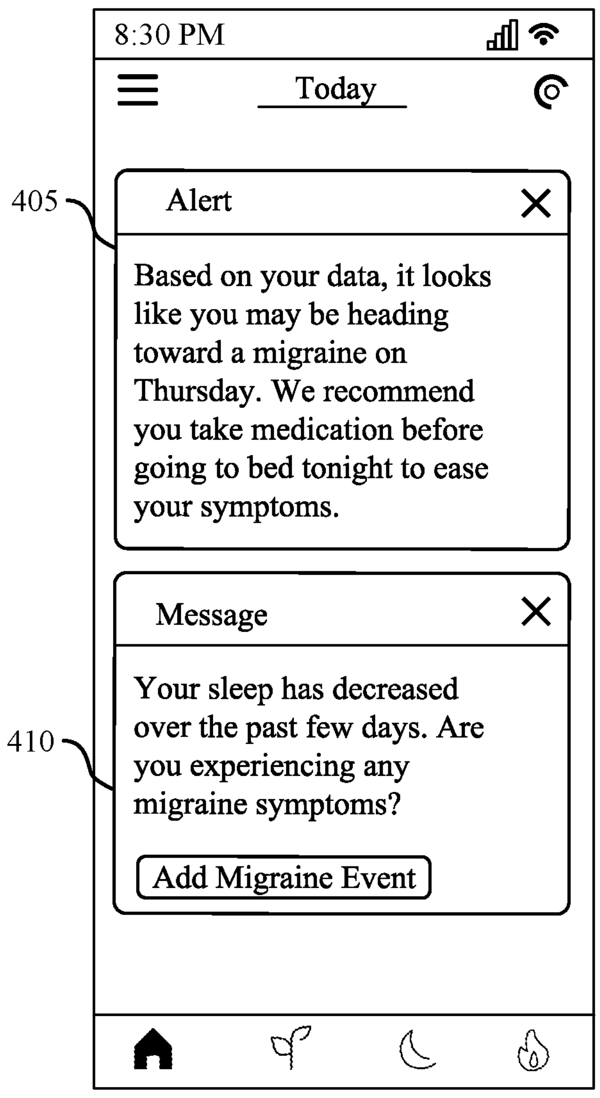
FIG. 4 shows an example of a graphical user interface (GUI) that supports techniques for migraine detection using a wearable device in accordance with aspects of the present disclosure.

FIG. 4 shows an illustrative example of a GUI 400 that supports techniques for migraine detection using a wearable device in accordance with aspects of the present disclosure. The GUI 400 may implement, or be implemented by, aspects of the system 100, the system 200, the data diagrams 300, or any combination thereof. For example, the GUI 400 may include an example of the GUI included within a user device 106, as described with reference to FIG. 2. Although the GUI 400 is illustrated to include specific icons, messages, and the like, in some examples, the GUI 400 may display one or more other messages or icons related to a wearable device and/or migraine prediction.

In some examples, a system (e.g., a system including a wearable device and a user device, such as the system 100 and the system 200) may determine that a user of a wearable device may experience a migraine. For example, the system may determine that a correlation between a decrease in REM sleep time, total sleep time, and/or body temperature may be indicative of migraine onset, as described with reference to FIG. 3. The system may determine to display a message via a GUI 400 of a user device (e.g., a user device paired with the wearable device or another user device) based on determining that the user may experience a migraine.

In some examples, the GUI 400 may display a message 405 alerting the user that the user may experience a migraine in the future (e.g., one or two days in the future). The message 405 may provide the user with a day or time during which the user may experience migraine symptoms. In some examples, the message 405 may provide a recommendation to the user in response to predicting that the user may experience a migraine. For example, the message 405 may provide a recommendation for the user to take migraine medication (e.g., including a time at which the user may take the migraine medication). The recommendation may be based on a predicted effectiveness of the migraine medication when taken at a certain time. That is, the system may determine that the migraine medication may be effective when taken ~8 hours before migraine onset, and may recommend via the message 405 the time period during which to take the migraine medication.

In some examples, a user device associated with a third party (e.g., a caretaker of the user) may display the message 405 via a GUI 400 of the third party user device. As an illustrative example, the system may cause a GUI 400 of a parent of the user to display a message 405 alerting the parent that the user may experience a migraine during a time period (e.g., and providing a recommendation, such as a recommended time at which to administer migraine medication to the user).

Additionally, or alternatively, the GUI 400 may display a message 410 requesting for user input regarding a migraine. For example, the message 410 may prompt the user to input data into an application associated with the user device and the wearable device. As an illustrative example, the message 410 may prompt the user to add a migraine event tag. The migraine event tag may be associated with a timestamp and/or a set of physiological data collected by the wearable device prior to the timestamp. In some examples, the system may use the set of physiological data to train a machine learning model to more accurately predict migraine symptoms (e.g., as described with reference to FIG. 3). For example, if the user indicates that the user is experiencing a migraine, the system may determine that the set of physiological data is indicative of migraine onset. If the user indicates that the user is not experiencing a migraine, the system may determine that the set of physiological data is not indicative of migraine onset.

In some examples, the GUI 400 may display information related to one or more migraine event tags added by the user. For example, the GUI 400 may display a timeline or frequency of tagged migraine events, a severity of tagged migraine events (e.g., a severity input by the user in response to a message 410 on the GUI 400), or one or more other events and/or event tags that are correlated with migraine events (e.g., exercise, alcohol intake, caffeine intake, menstrual cycles, stress levels, and so on measured by the wearable device or input by the user).

For example, the system may determine that an increase in caffeine intake of the user is correlated with an onset of migraine symptoms based on the user inputting a caffeine intake event tag prior to inputting a migraine event tag. In some examples, the GUI 400 may display (e.g., via the message 405) a recommendation regarding the correlated events or event tags. For example, the message 405 may recommend for the user to avoid caffeine intake if the system determines that an increase in caffeine intake is correlated with migraine events.

FIG. 5 shows a flowchart illustrating a method 500 that supports techniques for migraine detection using a wearable device in accordance with aspects of the present disclosure. The operations of the method 500 may be implemented by a user device or its components as described herein. For example, the operations of the method 500 may be performed by a user device as described with reference to FIGS. 1 through 4. In some examples, a user device may execute a set of instructions to control the functional elements of the user device to perform the described functions. Additionally, or alternatively, the user device may perform aspects of the described functions using special-purpose hardware.

At 505, the method may include acquiring physiological data from a user using a wearable device, the physiological data comprising PPG data collected via one or more light-emitting components and one or more light-receiving components of the wearable device, wherein the physiological data is acquired throughout a first time interval that includes one or more sleep periods of the user. The operations of 505 may be performed in accordance with examples as disclosed herein.

At 510, the method may include classifying, using a first machine learning model trained to perform sleep stage classification, the physiological data collected during the one or more sleep periods into a plurality of sleep stages, the plurality of sleep stages comprising at least a REM sleep stage. The operations of 510 may be performed in accordance with examples as disclosed herein.

At 515, the method may include inputting the physiological data into a second machine learning model, the second machine learning model trained to predict migraine onset based on a plurality of features within a training physiological dataset associated with a plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users. The operations of 515 may be performed in accordance with examples as disclosed herein.

At 520, the method may include generating, using the second machine learning model, a migraine prediction metric based at least in part on the plurality of features within the physiological data during the first time interval, the migraine prediction metric associated with a relative likelihood that the user will experience a migraine during a subsequent time interval. The operations of 520 may be performed in accordance with examples as disclosed herein.

At 525, the method may include transmitting an instruction to a GUI of a user device associated with the wearable device, the instruction configured to cause the GUI to display information associated with the migraine prediction metric. The operations of 525 may be performed in accordance with examples as disclosed herein.

Figure 6:
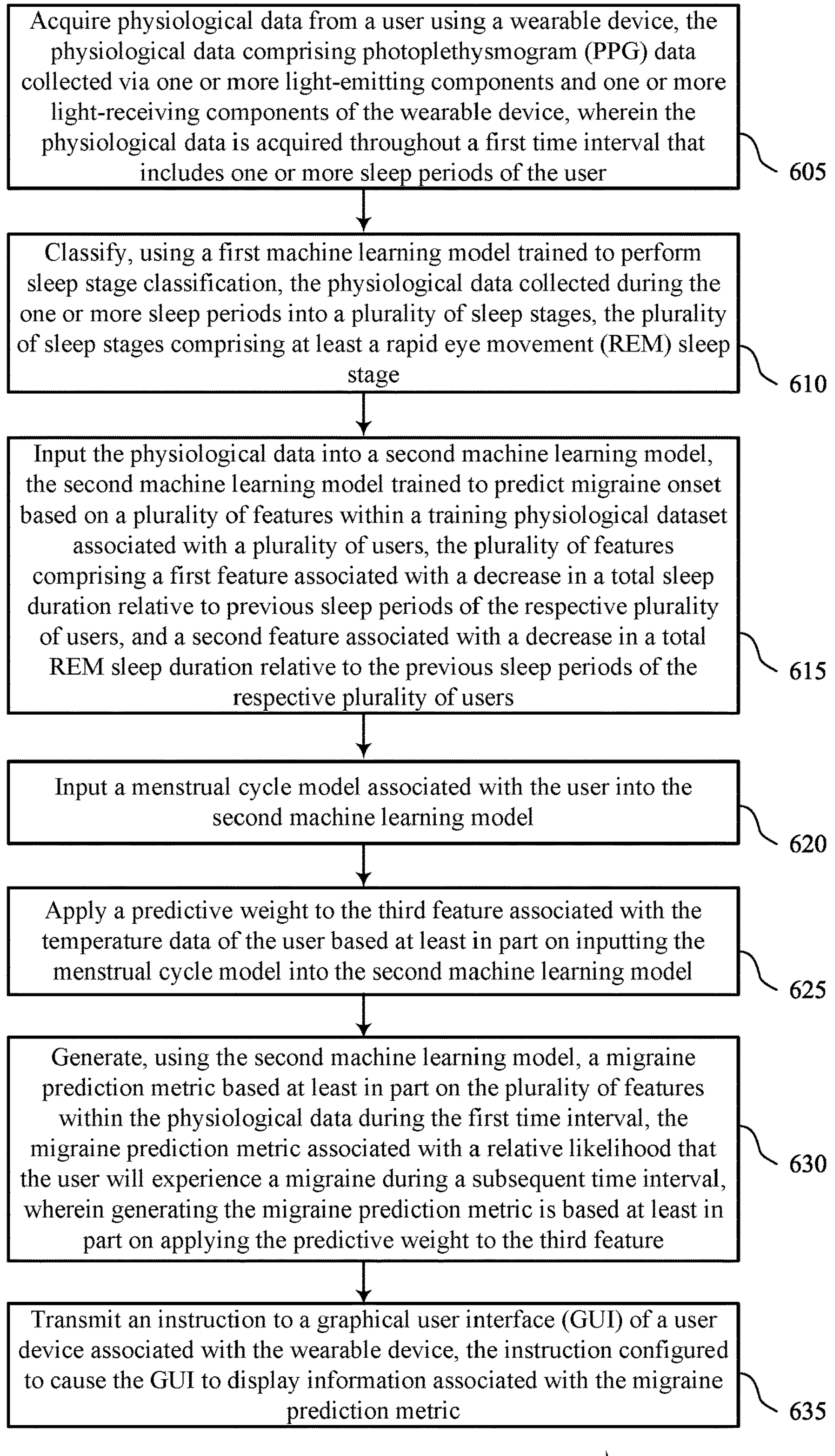

FIG. 6 shows a flowchart illustrating a method 600 that supports techniques for migraine detection using a wearable device in accordance with aspects of the present disclosure. The operations of the method 600 may be implemented by a user device or its components as described herein. For example, the operations of the method 600 may be performed by a user device as described with reference to FIGS. 1 through 4. In some examples, a user device may execute a set of instructions to control the functional elements of the user device to perform the described functions. Additionally, or alternatively, the user device may perform aspects of the described functions using special-purpose hardware.

At 605, the method may include acquiring physiological data from a user using a wearable device, the physiological data comprising PPG data collected via one or more light-emitting components and one or more light-receiving components of the wearable device, wherein the physiological data is acquired throughout a first time interval that includes one or more sleep periods of the user. The operations of 605 may be performed in accordance with examples as disclosed herein.

At 610, the method may include classifying, using a first machine learning model trained to perform sleep stage classification, the physiological data collected during the one or more sleep periods into a plurality of sleep stages, the plurality of sleep stages comprising at least a REM sleep stage. The operations of 610 may be performed in accordance with examples as disclosed herein.

At 615, the method may include inputting the physiological data into a second machine learning model, the second machine learning model trained to predict migraine onset based on a plurality of features within a training physiological dataset associated with a plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users. The operations of 615 may be performed in accordance with examples as disclosed herein.

At 620, the method may include inputting a menstrual cycle model associated with the user into the second machine learning model. The operations of 620 may be performed in accordance with examples as disclosed herein.

At 625, the method may include applying a predictive weight to the third feature associated with the temperature data of the user based at least in part on inputting the menstrual cycle model into the second machine learning model. The operations of 625 may be performed in accordance with examples as disclosed herein.

At 630, the method may include generating, using the second machine learning model, a migraine prediction metric based at least in part on the plurality of features within the physiological data during the first time interval, the migraine prediction metric associated with a relative likelihood that the user will experience a migraine during a subsequent time interval, wherein generating the migraine prediction metric is based at least in part on applying the predictive weight to the third feature. The operations of 630 may be performed in accordance with examples as disclosed herein.

At 635, the method may include transmitting an instruction to a GUI of a user device associated with the wearable device, the instruction configured to cause the GUI to display information associated with the migraine prediction metric. The operations of 635 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include acquiring physiological data from a user using a wearable device, the physiological data comprising PPG data collected via one or more light-emitting components and one or more light-receiving components of the wearable device, wherein the physiological data is acquired throughout a first time interval that includes one or more sleep periods of the user, classifying, using a first machine learning model trained to perform sleep stage classification, the physiological data collected during the one or more sleep periods into a plurality of sleep stages, the plurality of sleep stages comprising at least a REM sleep stage, inputting the physiological data into a second machine learning model, the second machine learning model trained to predict migraine onset based on a plurality of features within a training physiological dataset associated with a respective plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users, generating, using the second machine learning model, a migraine prediction metric based at least in part on the plurality of features within the physiological data during the first time interval, the migraine prediction metric associated with a relative likelihood that the user will experience a migraine during a subsequent time interval, and transmitting an instruction to a GUI of a user device associated with the wearable device, the instruction configured to cause the GUI to display information associated with the migraine prediction metric.

An apparatus is described. The apparatus may include one or more memories storing processor executable code, and one or more processors coupled with the one or more memories. The one or more processors may individually or collectively be operable to execute the code to cause the apparatus to acquire physiological data from a user using a wearable device, the physiological data comprising photoplethysmogram (PPG) data collected via one or more light-emitting components and one or more light-receiving components of the wearable device, wherein the physiological data is acquired throughout a first time interval that includes one or more sleep periods of the user, classify, using a first machine learning model trained to perform sleep stage classification, the physiological data collected during the one or more sleep periods into a plurality of sleep stages, the plurality of sleep stages comprising at least a rapid eye movement (REM) sleep stage, input the physiological data into a second machine learning model, the second machine learning model trained to predict migraine onset based on a plurality of features within a training physiological dataset associated with a respective plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users, generate, using the second machine learning model, a migraine prediction metric based at least in part on the plurality of features within the physiological data during the first time interval, the migraine prediction metric associated with a relative likelihood that the user will experience a migraine during a subsequent time interval, and transmit an instruction to a GUI of a user device associated with the wearable device, the instruction configured to cause the GUI to display information associated with the migraine prediction metric.

Another apparatus is described. The apparatus may include means for acquiring physiological data from a user using a wearable device, the physiological data comprising PPG data collected via one or more light-emitting components and one or more light-receiving components of the wearable device, wherein the physiological data is acquired throughout a first time interval that includes one or more sleep periods of the user, means for classifying, using a first machine learning model trained to perform sleep stage classification, the physiological data collected during the one or more sleep periods into a plurality of sleep stages, the plurality of sleep stages comprising at least a REM sleep stage, means for inputting the physiological data into a second machine learning model, the second machine learning model trained to predict migraine onset based on a plurality of features within a training physiological dataset associated with a respective plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users, means for generating, using the second machine learning model, a migraine prediction metric based at least in part on the plurality of features within the physiological data during the first time interval, the migraine prediction metric associated with a relative likelihood that the user will experience a migraine during a subsequent time interval, and means for transmitting an instruction to a GUI of a user device associated with the wearable device, the instruction configured to cause the GUI to display information associated with the migraine prediction metric.

A non-transitory computer-readable medium storing code is described. The code may include instructions executable by one or more processors to acquire physiological data from a user using a wearable device, the physiological data comprising PPG data collected via one or more light-emitting components and one or more light-receiving components of the wearable device, wherein the physiological data is acquired throughout a first time interval that includes one or more sleep periods of the user, classify, using a first machine learning model trained to perform sleep stage classification, the physiological data collected during the one or more sleep periods into a plurality of sleep stages, the plurality of sleep stages comprising at least a REM sleep stage, input the physiological data into a second machine learning model, the second machine learning model trained to predict migraine onset based on a plurality of features within a training physiological dataset associated with a respective plurality of users, the plurality of features comprising a first feature associated with a decrease in a total sleep duration relative to previous sleep periods of the respective plurality of users, and a second feature associated with a decrease in a total REM sleep duration relative to the previous sleep periods of the respective plurality of users, generate, using the second machine learning model, a migraine prediction metric based at least in part on the plurality of features within the physiological data during the first time interval, the migraine prediction metric associated with a relative likelihood that the user will experience a migraine during a subsequent time interval, and transmit an instruction to a GUI of a user device associated with the wearable device, the instruction configured to cause the GUI to display information associated with the migraine prediction metric.

In some examples of the method, apparatus, and non-transitory computer-readable medium described herein, the physiological data further comprises temperature data collected via one or more temperature sensors of the wearable device, the plurality of features used by the second machine learning model to predict migraine onset further comprise a third feature associated with a decrease in temperature data relative to baseline temperature data of the respective plurality of users, and the migraine prediction metric may be generated based at least in part on inputting the temperature data into the second machine learning model and based at least in part on the third feature within the temperature data.

Some examples of the method, apparatus, and non-transitory computer-readable medium described herein may further include operations, features, means, or instructions for generating the migraine prediction metric based at least in part on the first feature, the second feature, and the third feature occurring within the physiological data of the user at approximately a same time.

In some examples of the method, apparatus, and non-transitory computer-readable medium described herein, the second machine learning model may be configured to identify that the first feature, the second feature, and the third feature occur at approximately the same time based at least in part on the first feature, the second feature, and the third feature occurring within a same sleep day.

Some examples of the method, apparatus, and non-transitory computer-readable medium described herein may further include operations, features, means, or instructions for inputting a menstrual cycle model associated with the user into the second machine learning model and applying a predictive weight to the third feature associated with the temperature data of the user based at least in part on inputting the menstrual cycle model into the second machine learning model, wherein generating the migraine prediction metric may be based at least in part on applying the predictive weight to the third feature.

Some examples of the method, apparatus, and non-transitory computer-readable medium described herein may further include operations, features, means, or instructions for determining an estimation of the subsequent time interval that the migraine may be predicted to occur based at least in part on relative timings of the first feature, the second feature, and the third feature, wherein the instruction may be configured to cause the GUI to display the estimation of the subsequent time interval.

Some examples of the method, apparatus, and non-transitory computer-readable medium described herein may further include operations, features, means, or instructions for determine a third time interval for performing one or more preventative measures for mitigating or preventing the migraine during the subsequent time interval based at least in part on a first timing of the plurality of features within the physiological data and a second timing of the subsequent time interval, wherein the third time interval may be between the first time interval and the subsequent time interval, wherein the instruction may be configured to cause the GUI to display an indication of the third time interval and a recommendation to perform the one or more preventative measures during the third time interval.

Some examples of the method, apparatus, and non-transitory computer-readable medium described herein may further include operations, features, means, or instructions for receiving baseline physiological data associated with the user, the baseline physiological data collected during a reference time interval prior to the first time interval, receiving, via the wearable device, the user device, or both, a user input indicating one or more tags associated with one or more migraines experienced by the user during the reference time interval, and training the second machine learning model to predict migraines for the user based at least in part on the plurality of features within the baseline physiological data and the one or more tags, wherein generating the migraine prediction metric associated with the user may be based at least in part on training the second machine learning model.

Some examples of the method, systems, and non-transitory computer-readable medium described herein may further include operations, features, means, or instructions for determining a third time interval for performing one or more preventative measures for mitigating or preventing the migraine during the subsequent time interval based at least in part on a first timing of the plurality of features within the physiological data and a second timing of the subsequent time interval, wherein the third time interval may be between the first time interval and the subsequent time interval, wherein the instruction may be configured to cause the GUI to display an indication of the third time interval and a recommendation to perform the one or more preventative measures during the third time interval.

Some examples of the method, systems, and non-transitory computer-readable medium described herein may further include operations, features, means, or instructions for identifying one or more additional features associated with prediction of migraines for the user based at least in part on training the second machine learning model using the baseline physiological data and the one or more tags, wherein generating the migraine prediction metric may be based at least in part on the one or more additional features within the physiological data during the first time interval.

In some examples of the method, systems, and non-transitory computer-readable medium described herein, generation of the migraine prediction metric and transmission of the instruction the GUI may be performed prior to onset of symptoms associated with the migraine.

In some examples of the method, systems, and non-transitory computer-readable medium described herein, the wearable device comprises a wearable ring device.

In some examples of the method, systems for predicting migraine onset, and non-transitory computer-readable medium described herein, the wearable device comprises wrist-worn wearable device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for predicting migraine onset, comprising:

a wearable device configured to acquire physiological data from a user, the physiological data comprising photoplethysmogram (PPG) data collected via one or more light-emitting components and one or more light-receiving components of the wearable device, wherein the physiological data is collected throughout a first time interval that includes one or more sleep periods of the user; and one or more processors communicatively coupled with the wearable device, wherein the one or more processors are configured to:

receive the physiological data acquired via the wearable device via one or more electronic signals;

classify, using a first machine learning model trained to perform sleep stage classification, the physiological data collected during the one or more sleep periods into a plurality of sleep stages, the plurality of sleep stages comprising at least a rapid eye movement (REM) sleep stage;

input the physiological data into a second machine learning model, the second machine learning model trained to predict migraine onset based on a plurality of features within a training physiological dataset associated with one or more users, the plurality of features comprising a first feature associated with a decrease in a total sleep duration relative to previous sleep periods of the respective one or more users, and a second feature associated with a decrease in a total REM sleep duration relative to the previous sleep periods of the respective one or more users;

generate, using the second machine learning model, a migraine prediction metric based at least in part on the plurality of features within the physiological data during the first time interval, the migraine prediction metric associated with a relative likelihood that the user will experience a migraine during a subsequent time interval; and transmit an instruction to a graphical user interface (GUI) of a user device associated with the wearable device, the instruction configured to cause the GUI to display information associated with the migraine prediction metric.

2. The system of claim 1, wherein the physiological data further comprises temperature data collected via one or more temperature sensors of the wearable device, wherein the plurality of features used by the second machine learning model to predict migraine onset further comprise a third feature associated with a decrease in temperature data relative to baseline temperature data of the respective one or more users, and wherein the migraine prediction metric is generated based at least in part on inputting the temperature data into the second machine learning model and based at least in part on the third feature within the temperature data.

3. The system of claim 2, wherein the one or more processors are further configured to:

generate the migraine prediction metric based at least in part on the first feature, the second feature, and the third feature occurring within the physiological data of the user at approximately a same time.

4. The system of claim 3, wherein the second machine learning model is configured to identify that the first feature, the second feature, and the third feature occur at approximately the same time based at least in part on the first feature, the second feature, and the third feature occurring within a same sleep day.

5. The system of claim 2, wherein the one or more processors are further configured to:

input a menstrual cycle model associated with the user into the second machine learning model; and apply a predictive weight to the third feature associated with the temperature data of the user based at least in part on inputting the menstrual cycle model into the second machine learning model, wherein generating the migraine prediction metric is based at least in part on applying the predictive weight to the third feature.

6. The system of claim 2, wherein the one or more processors are further configured to:

determine an estimation of the subsequent time interval that the migraine is predicted to occur based at least in part on relative timings of the first feature, the second feature, and the third feature, wherein the instruction is configured to cause the GUI to display the estimation of the subsequent time interval.

7. The system of claim 1, wherein the one or more processors are further configured to:

determine a third time interval for performing one or more preventative measures for mitigating or preventing the migraine during the subsequent time interval based at least in part on a first timing of the plurality of features within the physiological data and a second timing of the subsequent time interval, wherein the third time interval is between the first time interval and the subsequent time interval, wherein the instruction is configured to cause the GUI to display an indication of the third time interval and a recommendation to perform the one or more preventative measures during the third time interval.

8. The system of claim 1, wherein the one or more processors are further configured to:

receive baseline physiological data associated with the user, the baseline physiological data collected during a reference time interval prior to the first time interval;

receive, via the wearable device, the user device, or both, a user input indicating one or more tags associated with one or more migraines experienced by the user during the reference time interval; and train the second machine learning model to predict migraines for the user based at least in part on the plurality of features within the baseline physiological data and the one or more tags, wherein generating the migraine prediction metric associated with the user is based at least in part on training the second machine learning model.

9. The system of claim 8, wherein the one or more processors are further configured to:

identify one or more additional features associated with prediction of migraines for the user based at least in part on training the second machine learning model using the baseline physiological data and the one or more tags, wherein generating the migraine prediction metric is based at least in part on the one or more additional features within the physiological data during the first time interval.

10. The system of claim 1, wherein generation of the migraine prediction metric and transmission of the instruction the GUI is performed prior to onset of symptoms associated with the migraine.

11. The system of claim 1, wherein the wearable device comprises a wearable ring device.

12. The system of claim 1, wherein the wearable device comprises wrist-worn wearable device.

13. A method for predicting migraine onset, comprising:

acquiring physiological data from a user using a wearable device, the physiological data comprising photoplethysmogram (PPG) data collected via one or more light-emitting components and one or more light-receiving components of the wearable device, wherein the physiological data is acquired throughout a first time interval that includes one or more sleep periods of the user;

classifying, using a first machine learning model trained to perform sleep stage classification, the physiological data collected during the one or more sleep periods into a plurality of sleep stages, the plurality of sleep stages comprising at least a rapid eye movement (REM) sleep stage;

inputting the physiological data into a second machine learning model, the second machine learning model trained to predict migraine onset based on a plurality of features within a training physiological dataset associated with one or more users, the plurality of features comprising a first feature associated with a decrease in a total sleep duration relative to previous sleep periods of the respective one or more users, and a second feature associated with a decrease in a total REM sleep duration relative to the previous sleep periods of the respective one or more users;

generating, using the second machine learning model, a migraine prediction metric based at least in part on the plurality of features within the physiological data during the first time interval, the migraine prediction metric associated with a relative likelihood that the user will experience a migraine during a subsequent time interval; and transmitting an instruction to a graphical user interface (GUI) of a user device associated with the wearable device, the instruction configured to cause the GUI to display information associated with the migraine prediction metric.

14. The method of claim 13, wherein the physiological data further comprises temperature data collected via one or more temperature sensors of the wearable device, wherein the plurality of features used by the second machine learning model to predict migraine onset further comprise a third feature associated with a decrease in temperature data relative to baseline temperature data of the respective one or more users, and wherein the migraine prediction metric is generated based at least in part on inputting the temperature data into the second machine learning model and based at least in part on the third feature within the temperature data.

15. The method of claim 14, further comprising:

generating the migraine prediction metric based at least in part on the first feature, the second feature, and the third feature occurring within the physiological data of the user at approximately a same time.

16. The method of claim 15, wherein the second machine learning model is configured to identify that the first feature, the second feature, and the third feature occur at approximately the same time based at least in part on the first feature, the second feature, and the third feature occurring within a same sleep day.

17. The method of claim 14, further comprising:

inputting a menstrual cycle model associated with the user into the second machine learning model; and applying a predictive weight to the third feature associated with the temperature data of the user based at least in part on inputting the menstrual cycle model into the second machine learning model, wherein generating the migraine prediction metric is based at least in part on applying the predictive weight to the third feature.

18. The method of claim 14, further comprising:

determining an estimation of the subsequent time interval that the migraine is predicted to occur based at least in part on relative timings of the first feature, the second feature, and the third feature, wherein the instruction is configured to cause the GUI to display the estimation of the subsequent time interval.

19. The method of claim 13, further comprising:

determine a third time interval for performing one or more preventative measures for mitigating or preventing the migraine during the subsequent time interval based at least in part on a first timing of the plurality of features within the physiological data and a second timing of the subsequent time interval, wherein the third time interval is between the first time interval and the subsequent time interval, wherein the instruction is configured to cause the GUI to display an indication of the third time interval and a recommendation to perform the one or more preventative measures during the third time interval.

20. The method of claim 13, further comprising:

receiving baseline physiological data associated with the user, the baseline physiological data collected during a reference time interval prior to the first time interval;

receiving, via the wearable device, the user device, or both, a user input indicating one or more tags associated with one or more migraines experienced by the user during the reference time interval; and training the second machine learning model to predict migraines for the user based at least in part on the plurality of features within the baseline physiological data and the one or more tags, wherein generating the migraine prediction metric associated with the user is based at least in part on training the second machine learning model.

* * * * *